United States Patent
Higa et al.

(10) Patent No.: US 6,391,900 B1
(45) Date of Patent: May 21, 2002

(54) CYTOTOXIC TRIS(OXAZOLE)-CONTAINING MACROLIDES

(75) Inventors: Tatsuo Higa; Dolores Garcia Gravalos; Jose Luis Fernandez Puentes, all of Onzonilla (ES)

(73) Assignee: Instituto Biomar S.A., Leon (ES)

( * ) Notice: Subject to any disclaimer, the term of this patent is extended or adjusted under 35 U.S.C. 154(b) by 0 days.

(21) Appl. No.: 09/601,146

(22) PCT Filed: Jan. 27, 1999

(86) PCT No.: PCT/GB99/00277

§ 371 Date: Jan. 12, 2001

§ 102(e) Date: Jan. 12, 2001

(87) PCT Pub. No.: WO99/37653

PCT Pub. Date: Jul. 29, 1999

(30) Foreign Application Priority Data

Jan. 27, 1998 (GB) ............................................. 9801741

(51) Int. Cl.$^7$ ....................... A61P 35/00; A61K 31/424; A61K 31/395; C07D 498/22
(52) U.S. Cl. ........................................ 514/375; 540/469
(58) Field of Search ........................... 540/469; 514/375

(56) References Cited

U.S. PATENT DOCUMENTS 5,760,065 A  6/1998 Nonomura et al. ......... 514/374

FOREIGN PATENT DOCUMENTS

EP        0 729 950 A1   9/1995 ................. 263/34

OTHER PUBLICATIONS

Faulkner, D. *Nat. Prod. Rep.* 1997, 14, 259–302.
Scheuer, P.J. et al., *J. Am. Chem. Soc.* 1986, 108, 846–847.
Fusetani, N. et al., *J. Am. Chem. Soc.*, 1986, 108, 847–849.
*Marine Biotechnology*, Vol. 1, Ed. By David H. Attaway and Oskar R. Zaborsky, Plenum Press, New York 1993, pp. 211–213.
Raymond J. Bergeron et al., "Antineoplastic and Antiherpetic Activity of Spermidine Catecholamide Iron Chelators", *Biochem. Bioph. Res. Comm.* 1984, 121, 848–854.
Fusetani, N. et al., *J. Org. Chem.*, 1989, 54, 1360–1364.

*Primary Examiner*—Mark L Berch
*Assistant Examiner*—Kahsay Habte
(74) *Attorney, Agent, or Firm*—Ernest V. Linek; Banner & Witcoff, Ltd.

(57) ABSTRACT

The present invention discloses new cytotoxic tris(oxazole)-containing macrolides having the formula:

(I)

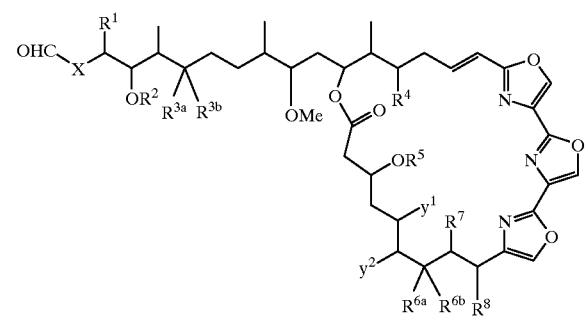

wherein X represents a lower alkyl; $R^1$ and $R^2$ represent hydrogen or lower alkyl; $R^{3a}$ represents hydrogen, and $R^{3b}$ represents

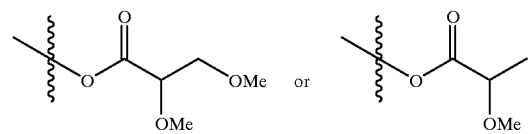

or $R^{3a}$ and $R^{3b}$ together represent oxygen; $R^4$ represents hydrogen, lower alkoxy or lower alkyl; $R^5$ represents hydrogen, carbamoyl, or lower alkanoyl; $R^{6a}$ represents hydrogen, and $R^{6b}$ represents hydroxy, or $R^{6a}$ and $R^{6b}$ together represent oxygen; $R^7$ represents hydrogen, lower alkyl, or hydroxymethyl; $R^8$ represents lower alkoxy or lower alkyl; $Y^1$ represents hydrogen or methyl, and $Y^2$ represents hydrogen, or $Y^1$ and $Y^2$ together represent a double bond. Also disclose are methods for treating mammals using the macrolides and pharmaceutical preparations including the macrolides.

10 Claims, No Drawings

CYTOTOXIC TRIS(OXAZOLE)-CONTAINING MACROLIDES

The present invention relates to new cytotoxic tris (oxazole)-containing macrolides obtained by chemical modification of marine natural products.

BACKGROUND OF THE INVENTION

Marine organisms, especially soft corals, sponges and tunicates, provide many secondary metabolites and exhibit a varying degree of biological activity (Reference 1). An important family of these metabolites is the cytotoxic tris (oxazole)-containing macrolide family; in 1986 it was reported the structure of the three first tris(oxazole)-containing macrolides: Ulapualide A and B (Reference 2) and Kabiramide C (Reference 3).

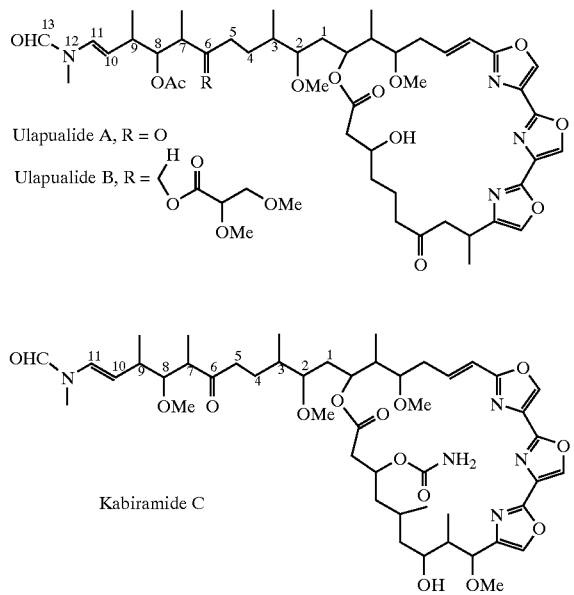

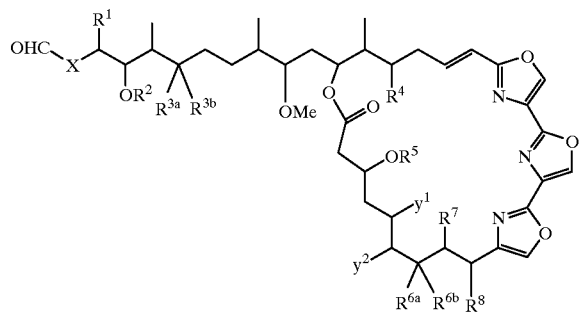

Since then, over 30 additional tris(oxazole)containing macrolides have been published (Reference 4).

SUMMARY OF THE INVENTION

The present invention relates to now cytotoxic tris (oxazole)-containing macrolides having the formula (I):

(I)

wherein X represents a lower alkyl; $R^1$ and $R^2$ represent hydrogen or lower alkyl; $R^{3a}$ represents hydrogen, and $R^{3b}$ represents

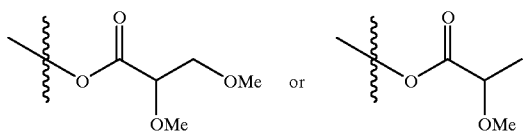

or $R^{3a}$ and $R^{3b}$ together represent oxygen; $R^4$ represents hydrogen, lower alkoxy or lower alkyl; $R^5$ represents hydrogen, carbarnoyl, or lower alkanoyl; $R^{6a}$ represents hydrogen, and $R^{6b}$ represents hydroxy, or $R^{6a}$ and $R^{6b}$ together represent oxygen; $R^7$ represents hydrogen, lower alkyl, or hydroxymethyl; $R^8$ represents lower alkoxy or lower alkyl; $Y^1$ represents hydrogen or methyl, and $y^2$ represents hydrogen, or $Y^1$ and $Y^2$ together represent a double bond.

In the definitions of the groups in formula (1), the lower alkyl and the lower alkyl moiety of the lower alkanoyl or of the lower alkoxy mean a straight-chain or branched alkyl group having 1 to 6 carbon atoms such as methyl, ethyl, propyl, isopropyl, butyl, isobutyl, sec-butyl, tert-butyl, pentyl, neopentyl and hexyl.

More particularly, the present invention relates to HA-1 and TH-2, with structural formulas:

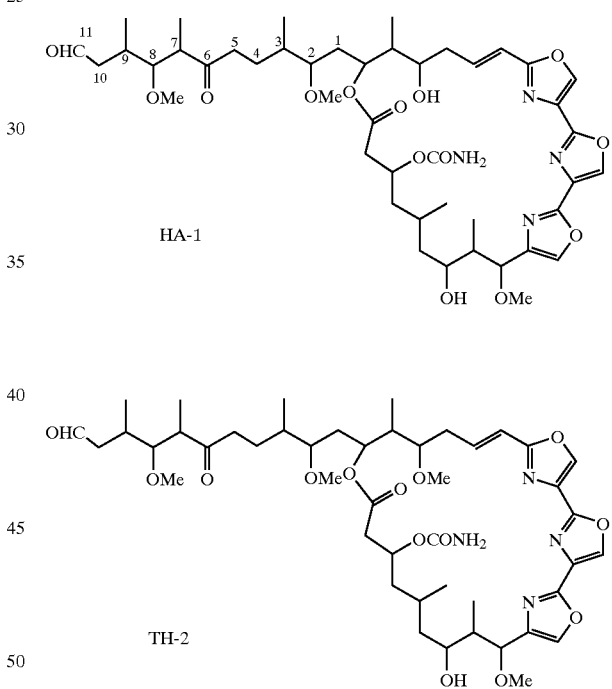

HA-1 and TH-2 were obtained by chemical modification of the known Kabiramide B and C respectively.

HA-1 and TH-2 exhibit antitumor activity. In particular, HA-1 and TH-2 exhibit antitumor activity against cell lines derived from human solid tumors, such as human lung carcinoma, human colon carcinoma and human melanoma, and, the like, they are active against other tumor cell lines, like leukemia and lymphoma. These compounds, HA-1 and TH-2, have in vitro antitumor selectivity for solid tumors.

The present invention also relates to a method for treating a mammal affected by a malignant tumor sensitive to a compound with formula (I), which comprises administering to the affected individual a therapeutically effective amount of the compound with formula (I) or a pharmaceutical composition thereof.

The present invention further provides pharmaceutical compositions which contain as active ingredient a compound with formula (I), as well as a process for its preparation.

A further aspect of the invention is a method for preparing the compounds HA-1 and TH-2, which comprises chemical modification of Kabiramide B and C respectively.

Examples of pharmaceutical compositions include any solid (tablets, pills, capsules, granules, etc.) or liquid (solutioms, suspensions or emulsions) with suitable formulation of oral, topical or parenteral administration, and they may contain the pure compound or in combination with any carrier or other pharmacologically active compounds. These compositions may need to be sterile when administered parenterally.

The correct dosage of a pharmaceutical composition comprising compounds with formula (I), will vary according to the pharmaceutical formulation, the mode of application, and the particular situs, host and tumor being treated. Other factors like age, body weight, sex, diet, time of administration, rate of excretion, condition of the host, drug combinations, reaction sensitivities and severity of the disease shall be taken into account. Administration can be carried out continuously or periodically within the maximum tolerated dose.

Antitumour Activity

Cells were maintained in logarithmic phase of growth in Eagle's Minimum Essential Medium, with Earle's Balanced Salts, with 2.0 mM L-glutamine, with non-essential amino acids, without sodium bicarbonate EMEM/neaa); supplemented with 10% Fetal Calf Serum (FCS), $10^{-2}$ M sodium bicarbonate and 0.1 g/l penicillin-G+streptomycin sulfate.

A screening procedure has been carried out to determine and compare the antitumor activity of these compounds, using an adapted form of the method described by Bergeron et al. (Reference 5). The antitumor cells employed were P-388 (suspension culture of a lymphoid neoplasm from DBA/2 mouse), A-549 (monolayer culture of a human lung carcinoma), HT-29 (monolayer culture of a human colon carcinoma) and MEL-28 (monolayer culture of a human melanoma).

P-139 cells were seeded into 16 mm wells at $1\times10^4$ sells per well in 1 ml aliquots of MEM SFCS containing the indicated concentration of drug. A separate set of cultures without drug was seeded as control growth to ensure that cells remained in exponential phase of growth. All determinations were carried out in duplicate. After three days of incubation at 37° C., 10% $CO_2$ in a 98% humid atmosphere, an approximately $IC_{50}$ was determined by comparing the growth in wells with drug to the growth in wells control.

A-549, HT-29 and MEL-28 cells were seeded into 16 mm wells at $2\times10^4$ cells per well in 1 ml aliquots of MEM 10FCS containing the indicated concentration of drug. A separate set of cultures without drug was seeded as control growth to ensure that cells remained in exponential phase of growth. All determinations were carried out in duplicate. After three days of incubation at 37° C., 10% $CO_2$ in a 98% humid atmosphere, the wells were stained with 0.1% Crystal Violet. An approximately $IC_{50}$ was determined by comparing the growth in wells with drug to the growth in wells control.

The results of the in vitro cytotoxic assays for HA-1 and TH-2 with the celular lines P-388, A-549, XT-29 and MEL-28 are given in the following table;

| Compound | $IC_{50}(\mu M)$ | | | |
|---|---|---|---|---|
| | P-388 | A-549 | HT-29 | MEL-28 |
| HA-1 | 0.010 | 0.001 | 0.001 | 0.001 |
| TH-2 | 0.011 | 0.002 | 0.002 | 0.002 |

It is showed that these compounds, HA-1 and TH-2, with a terminal aldehyde methyl group have in vitro antitumor selectivity for solid timors like A-549, HT-29,and MEL-28.

Isolation of the known Kabiramide B and C

A sample of an unidentified black sponge (wet, 13.2 kg) was collected at Sichang Island, May 1997. Its $CH_2Cl_2$ portion (67 g) was separated first by silica vacuum flash chromatography (VFC, stepwise elution), then by Sephadex ($CH_2Cl_2$—MeOH, 1-1), and finally by reversed phase HPLC (MeOH—$H_2O$—EtOAc, 3-2-1) to give both Kabiramide B (Reference 6) (24.0 mg) and Kabiramide C (Reference 3) (35.0 mg).

Synthesis of HA-1

Compound HA-1 was preparated by treating Kabiramide B (24.0 mg) in 10 mL of aqueous acidic dioxane (0.5 N HCl-dioxane, 2–3) for 2 hr at 50° C. The crude product was separated on reversed phase HPLC to give 6.4 mg (28%) of compound HA-1 as a glass, and 7.1 mg (30%) of recovered Kabiramide B.

The NMR data for HA-1 are:

All chemical shifts are reported with respect to TMS ($\delta$=0 ppm).

$^1$H NMR (CDCl$_3$): $\delta$ 9.75 (1H, t, J=2.5 Hz), 8.10 (1H, s), 8.04 (1H, s), 7.59 (1H, s), 7.29 (1H, m), 6.33 (1H, d, J=16.0 Hz), 5.18 (1H, dt, J=2.0, 10.0 Hz), 5.02 (1H, dd, J=8.0, 12.0 Hz), 4.85 (1H, s), 4.15 (1H, m), 3.84 (1H, m), 3.45 (3H, s), 3.37 (3H, s), 3.30 (3H, s), 3.27 (1H, dd, J=4.0, 7.5 Hz), 3.07 (1H, m), 2.73 (1H, m), 2.62 (1H, m), 2.57 (1H, m), 2.53 (2H, m), 2.45 (1H, m), 2.43 (2H, m), 2.36 (1H, dd, J=2.0, 8.0 Hz), 2.25 (1H, m), 2.09 (1H, m), 1.85 (3H, m), 1.75 (1H, m), 1.72 (3H, m), 1.46 (2H, m), 1.35 (1H, m), 1.05 (3H, d, J=7.0 Hz), 1.02 (3H, d, J=7.0 Hz), 1.01 (3H, d, J=7.0 Hz), 0.97 (3H, d, J=7.0 Hz), 0.93 (3H, d, J=7.0 Hz), 0.83 (3H, d, J=7.0 Hz). $^{13}$C NMR (CDCl$_3$): $\delta$ 213.3 s, 201.8 d, 172.0 s, 163.9 s, 157.7 s, 156.5 s, 155.4 s, 145.5 d, 141.7 s, 137.2 d, 136.9 d, 135.7 d, 131.1 s, 129.8 s, 115.1 d, 87.5 d, 82.2 d, 78.2 d, 74.4 d, 73.5 d, 70.4 d, 68.2 d, 60.6 q, 57.9 q, 57.6 q, 48.7 t, 46.1 t, 45.3 t, 43.4 t, 42.8 t, 42.7 d, 41.7 t, 37.8 t, 37.3 d, 34.7 d, 34.6 t, 31.0 d, 25.3 t, 25.1 d, 18.3 q (2C), 15.6 q, 13.4 q, 10.6 q, 9.2 q. IR (CHCl$_3$) 3470, 3015, 1720, 1650, 1460, 1315, 1215, 915, 665 cm$^{-1}$.

Synthesis of TH-2

A mixture of Kabiramide C (35.0 mg) in 10 mL of 0.5 N HCl-dioxane (2–3) was stirred at 50° C. for 2 h. The mixture was partitioned between EtOAc and water, and the organic layer was concentrated The crude product was separated on reversed phase HPLC (MeCN—$H_2O$—EtOAc, 6-4-1) to give 11.0 mg (33%) of compound TH-2 as a glass, and 18.3 mg (52%) of recovered Kabiramide C.

The NMR data for TH-2 are:

All chemical shifts are reported with respect to TMS ($\delta$0 ppm).

$^1$H NMR (CDCl$_3$) δ 9.75 (1H, t, J=2.3 Hz), 8.09 (1H, s), 8.03 (1H, s), 7.58 (1H, d, J=1.0 Hz), 7.46 (1H, ddd, J=16.0, 9.5, 5.0 Hz), 6.29 (1H, d, J=16.0 Hz), 5.32 (1H, m), 5.17 (1H, t, J=10.5 Hz), 4.80 (1H, s), 3.84 (1H, m), 3.67 (1H, m), 3.45 (3H, s), 3.43 (3H, s), 3.33 (3H, s), 3.30 (3H, s), 3.27 (1H, m), 3.01 (1H, m), 2.81 (1H, m), 2.72 (1H, t, 8.0 Hz), 2.59 (1H, dd, J=14.3, 9.7 Hz), 2.52 (1H, m), 2.44 (1H, m), 2.41 (1H, m), 2.36 (1H, m), 2.32 (1H, m), 2.15 (1H, m), 1.85 (1H, m), 1.46 (1H, m), 1.34 (1H, m), 1.04 (3H, d, J=6.7 Hz), 1.01 (3H, d, J=7.0 Hz), 0.99 (3H, d, J=7.0 Hz), 0.94 (3H, d, J=7.0 Hz), 0.87 (3H, d, J=6.4 Hz), 0.83 (3H, d, J=7.0 Hz).
$^{13}$C NMR (CDCl$_3$) δ 213.4 s, 201.8 d, 171.6 s, 163.2 s, 157.3 s, 156.4 s, 155.4 s, 142.0 d, 141.4 s, 137.1 d, 136.8 d, 135.6 d, 131.1 s, 129.9 s, 115.5 d, 87.4 d, 82.0 d, 79.2 d, 78.3 d, 74.0 d, 73.3 d, 69.3 d, 60.6 q, 57.9 q, 57.6 q, 57.5 q, 48.6 t, 46.0 t, 45.0 t, 43.6 t, 42.9 t, 41,7 t, 40.4 d, 37.3 d, 34.5 d, 33.9 t, 32.9 t, 30.9 d, 25.0 d (2C), 18.2 q (2C), 15.5 q, 13.3 q, 10.7 q, 8.4 q.

References

1. Faulkner, D. *Nat.Prod.Rep.* 1997, 14, 259–302 and references therein.
2. Scheuer, P. J. et al. *J.Am.Chem.Soc.* 1986, 108, 846–847.
3. Fusetani, N. et al. *J.Am.Chem.Soc.* 1986, 108, 847–849.
4. *Marine Biotechnology*, Vol.1, Ed. by David H. Attaway and Oskar R. Zaborsky, Plenum Press, New York 1993, pp. 211–213, and references therein.
5. Raymond J. Bergeron, Paul F. Cavanaugh, Jr., Steven J. Kline, Robert G. Hughes, Jr., Gary T. Elliot and Carl W. Porter. Antineoplastic and antiherpetic activity of spernidine catecholamide iron chelators. *Biochem. Bioph. Res. Comm.* 1984, 121, 848–854.
6. Fusetani, N. et al. *J. Org. Chem.* 1989, 54, 1360–1363.

What is claimed is:

1. A compound having formula (I):

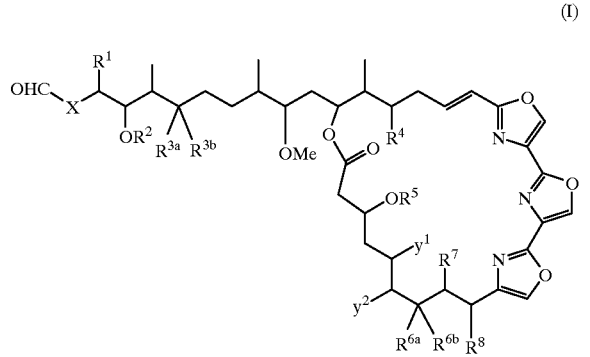

(I)

wherein X represents a methylene group;
R$^1$ and R$^2$ each represent a methyl group;
R$^{3a}$ and R$^{3b}$ together represent oxygen;
R$^4$ represents a hydroxy group or a methoxy group;
R$^5$ represents hydrogen, carbamoyl, or lower alkanoyl;
R$^{6a}$ represents hydrogen, and R$^{6b}$ represents hydroxy, or R$^{6a}$ and R$^{6b}$ together represent oxygen;
R$^7$ represents a methyl group;
R$^8$ represents a methoxy group;
y$^1$ represents a methyl group, and y$^2$ represents hydrogen.

2. A compound, HA-1, according to claim 1, having the following formula:

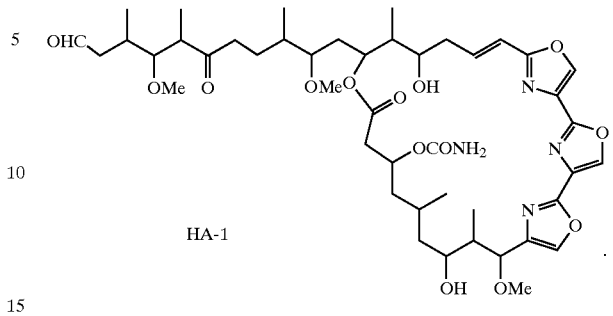

3. A compound, TH-2, according to claim 1, having the following formula:

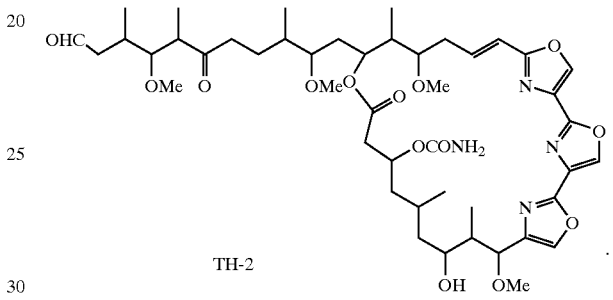

4. A method of treating a mammal affected by a malignant tumor sensitive to a compound having formula (I), as defined in claim 1, which comprises administering to the affected individual a therapeutically effective amount of the compound or a pharmaceutical composition thereof.

5. A method of treating a mammal affected by a malignant tumor sensitive to HA-1, as defined in claim 2, which comprises administering to the affected individual a therapeutically effective amount of HA-1 or a pharmaceutical composition thereof.

6. A method of treating a mammal affected by a malignant tumor sensitive to TH-2, as defined in claim 3, which comprises administering to the affected individual a therapeutically effective amount of TH-2 or a pharmaceutical composition thereof.

7. A pharmaceutical preparation which contains as an active ingredient a compound having formula (I), as defined in claim 1, together with a pharmaceutically acceptable carrier.

8. A pharmaceutical preparation which contains as an active ingredient HA-1 as defined in claim 2, or TH-2 as defined in claim 3, together with a pharmaceutically acceptable carrier.

9. A method for preparing HA-1 as defined in claim 2, said method comprising treating Kabiramide B with acid and recovering HA-1 from the reaction mixture.

10. A method for preparing TH-2 as defined in claim 3, said method comprising treating Kabiramide C with acid and recovering TH-2 from the reaction mixture.

* * * * *